(12) United States Patent
Sun et al.

(10) Patent No.: US 9,101,458 B2
(45) Date of Patent: Aug. 11, 2015

(54) DEVICE FOR TENDON AND LIGAMENT TREATMENT

(71) Applicant: LifeCell Corporation, Branchburg, NJ (US)

(72) Inventors: Wenquan Sun, Warrington, PA (US); Gary Monteiro, Branchburg, NJ (US)

(73) Assignee: LifeCell Corporation, Branchburg, NJ (US)

( * ) Notice: Subject to any disclaimer, the term of this patent is extended or adjusted under 35 U.S.C. 154(b) by 151 days.

(21) Appl. No.: 13/670,911

(22) Filed: Nov. 7, 2012

(65) Prior Publication Data

US 2013/0123920 A1   May 16, 2013

Related U.S. Application Data

(60) Provisional application No. 61/558,328, filed on Nov. 10, 2011.

(51) Int. Cl.
| | | |
|---|---|---|
| *A61F 2/08* | (2006.01) | |
| *A61K 38/18* | (2006.01) | |
| *A61K 38/19* | (2006.01) | |
| *A61L 27/54* | (2006.01) | |
| *A61L 27/36* | (2006.01) | |

(52) U.S. Cl.
CPC . *A61F 2/08* (2013.01); *A61K 38/18* (2013.01); *A61K 38/19* (2013.01); *A61L 27/3625* (2013.01); *A61L 27/3662* (2013.01); *A61L 27/3683* (2013.01); *A61L 27/54* (2013.01); *A61L 2300/404* (2013.01); *A61L 2300/414* (2013.01); *A61L 2300/426* (2013.01); *A61L 2300/64* (2013.01)

(58) Field of Classification Search
CPC .................................. A61F 2/08; A61F 2/0811
USPC ............................................ 623/11.11–13.2
See application file for complete search history.

(56) References Cited

U.S. PATENT DOCUMENTS

| | | | |
|---|---|---|---|
| 4,776,853 | A | 10/1988 | Klement et al. |
| 5,336,616 | A | 8/1994 | Livesey et al. |
| 5,460,962 | A | 10/1995 | Kemp |
| 6,206,931 | B1 | 3/2001 | Cook et al. |
| 6,358,284 | B1 | 3/2002 | Fearnot et al. |
| 2002/0183857 | A1* | 12/2002 | Yang .......................... 623/23.72 |
| 2003/0035843 | A1 | 2/2003 | Livesey et al. |
| 2004/0267362 | A1* | 12/2004 | Hwang et al. .............. 623/13.15 |
| 2006/0073592 | A1 | 4/2006 | Sun et al. |
| 2007/0293937 | A1 | 12/2007 | Biggs et al. |

(Continued)

FOREIGN PATENT DOCUMENTS

WO     WO 2005/009134 A1    2/2005

OTHER PUBLICATIONS

Barber et al.; "A Biomechanical Study of Achilles Tendon Repair Augmentation Using Graft-Jacket Matrix;" Foot & Ankle International; 29(3):329-333 (Mar. 2008).

(Continued)

*Primary Examiner* — Jason-Dennis Stewart
(74) *Attorney, Agent, or Firm* — McCarter & English, LLP; Matthew R. Van Eman

(57) ABSTRACT

Devices and methods for treating defects in connective tissue are provided along with methods for making such devices. The devices can include acellular arterial tissue matrices that facilitate regrowth of the damaged tissue.

19 Claims, 3 Drawing Sheets

(56) References Cited

U.S. PATENT DOCUMENTS

| | | | |
|---|---|---|---|
| 2008/0027542 A1* | 1/2008 | McQuillan et al. | 623/13.11 |
| 2009/0098176 A1* | 4/2009 | Helmus et al. | 424/422 |
| 2009/0306776 A1* | 12/2009 | Murray | 623/13.12 |
| 2010/0161054 A1* | 6/2010 | Park et al. | 623/13.14 |
| 2011/0046732 A1* | 2/2011 | Dyke et al. | 623/13.11 |
| 2011/0054588 A1 | 3/2011 | Xu et al. | |
| 2011/0135706 A1 | 6/2011 | Xu et al. | |
| 2011/0282448 A1* | 11/2011 | Paulos et al. | 623/13.11 |

OTHER PUBLICATIONS

Barber et al.; "Ultimate Tensile Failure Loads of a Human Dermal Allograft Rotator Cuff Augmentation;" The Journal of Arthroscopic and Related Surgery; 24(1):20-24 (Jan. 2008).

Beniker et al.; "The Use of Acellular Dermal Matrix as a Scaffold for Periosteum Replacement;" Orthopedics; 26(5/Suppl.):s591-s596 (May 2003).

Chen et al.; "Scaffolds for tendon and ligament repair: review of the efficacy of commercial products;" Expert Rev. Med. Devices; 6(1):61-73 (2009).

Coons et al.; "Tendon Graft Substitutes—Rotator Cuff Patches;" Sports Med. Arthrosc. Rev.; 14(3):185-190 (Sep. 2006).

Furukawa et al.; "Efficacy of interference screw and double-docking methods using palmaris longus and GraftJacket for medial collateral ligament reconstruction of the elbow;" J. Shoulder Elbow Surg.; 16(4):449-453 (Jul./Aug. 2007).

Ho et al.; "Allografts in the Treatment of Athletic Injuries of the Shoulder;" Sports Med. Arthrosc. Rev.; 15(3):149-157 (Sep. 2007).

Kummer et al.; "The Role of Graft Materials in Suture Augmentation for Tendon Repairs and Reattachment;" J. Biomed. Mater. Res. Part B: Appl. Biomater.; 74B:789-791 (2005).

Lee; "GraftJacket Augmentation of Chronic Achilles Tendon Ruptures;" Orthopedics; 27(1/Suppl.):s151-s153 (Jan. 2004).

Lee; "Achilles Tendon Repair with Acellular Tissue Graft Augmentation in Neglected Ruptures;" The Journal of Foot & Ankle Surgery; 46(6):451-455 (2007).

Lee; "A Preliminary Study on the Effects of Acellular Tissue Graft Augmentation in Acute Achilles Tendon Ruptures;" The Journal of Foot & Ankle Surgery; 47(1):8-12 (2008).

Liden et al.; "Histologic Evaluation of a 6-Month GraftJacket Matrix Biopsy Used for Achilles Tendon Augmentation;" J. Am. Podiatr. Med. Assoc.; 99(2):104-107 (2009).

Snyder et al.; "Histologic Evaluation of a Biopsy Specimen Obtained 3 Months After Rotator Cuff Augmentation With GraftJacket Matrix;" The Journal of Arthroscopic and Related Surgery; 25(3):329-333 (Mar. 2009).

Wong et al.; "Arthroscopic GraftJacket repair of rotator cuff tears;" J. Shoulder Elbow Surg.; 19:104-109 (2010).

Collins et al., "Cardiac Xenografts Between Primate Species Provide Evidence for the Importance of the α-Galactosyl Determinant in Hyperacute Rejection," J. Immunol. 154:5500-5510 (1995).

Galili et al., "Man, Apes, and Old World Monkeys Differ from Other Mammals in the Expression of α-Galactosyl Epitopes on Nucleated Cells," J. Biol. Chem., 263(33):17755-17762 (1988).

Galili et al., "Interaction between Human Natural Anti-α-Galactosyl Immunoglobulin G and Bacteria of the Human Flora," Infect. Immun., 56(7):1730-1737 (1988).

Galili et al., "Interaction of the natural anti-Gal antibody with α-galactosyl epitopes: a major obstacle for xenotransplantation in humans," Immunology Today, 14(10):480-482 (1993).

Good et al., "Identification of Carbohydrate Structures that Bind Human Antiporcine Antibodies: Implications for Discordant Xenografting in Humans," Transplant Proc., 24(2):559-562 (1992).

Hamadeh et al., "Human Natural Anti-Gal IgG Regulates Alternative Complement Pathway Activation on Bacterial Surfaces," J. Clin. Invest., 89:1223-1235 (1992).

International Patent Application No. PCT/US2012/063816: International Search Report and Written Opinion, dated Feb. 6, 2013. (13 pages).

Sandrin et al., "Anti-pig IgM antibodies in human serum react predominately with Gal(α1-3)Gal epitopes," Proc. Natl. Acad. Sci, USA, 90:11391-11395 (1993).

Xu et al., "A Porcine-Derived Acellular Dermal Scaffold That Supports Soft Tissue Regeneration: Removal of Terminal Galactose-α-(1,3)-Galactose and Retention of Matrix Structure," Tissue Engineering, 15(7):1807-1819 (2009).

Roy et al.; "Biomechanical proprieties of decellularized porcine common carotid arteries;" Am. J. Physiol. Heart Circ. Physiol.; 289:H1567-H1576 (2005).

* cited by examiner

DEVICE FOR TENDON AND LIGAMENT TREATMENT

This application claims priority to U.S. Provisional Application No. 61/558,328, filed Nov. 10, 2011, which is incorporated herein by reference in its entirety.

The present disclosure provides improved devices and methods for treating defects in connective tissue, such as tendons and ligaments.

The healing of tendons and ligaments is often associated with severe scarring. Furthermore, during the healing process, these various forms of connective tissue can sometimes adhere to other surrounding fibrous tissues. Scar formation and adhesion can limit the range of motion of the healed tissue and alter its material properties. Due to scar formation and/or adhesion within the joint, greater loading forces may be required to achieve desirable motion.

A conduit that protects the damaged tendon or ligament from further injury may expedite the healing process as well as minimize adhesion or scar formation. The conduit may aid the healing process by creating a protective environment and by minimizing the loss of growth factors or other natural cytokines that are released during healing.

In certain embodiments, a device for treating connective tissue is provided. The device comprises an arterial tissue matrix, wherein substantially all the native cells have been removed, and wherein the arterial tissue matrix is derived from an arterial section that has been cut across its length, and wherein the arterial tissue matrix includes an intact basement membrane present in the arterial section from which the tissue matrix is derived.

In certain embodiments, a method for preparing an arterial tissue matrix device is provided. The method comprises selecting an arterial section, removing substantially all the native cells from the section to obtain an arterial tissue matrix, without removing a luminal basement membrane from the arterial section, and cutting the arterial section across its length.

According to certain embodiments, a method for treating a tendon or ligament is provided. The method comprises selecting a tendon or ligament in need of treatment, selecting an arterial tissue matrix from which substantially all the native cells have been removed, and contacting the arterial tissue matrix with at least a portion of the tendon or ligament in need of treatment.

DESCRIPTION OF CERTAIN EXEMPLARY EMBODIMENTS

Reference will be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. In addition, terms such as "element" or "component" encompass both elements and components comprising one unit and elements and components that comprise more than one subunit, unless specifically stated otherwise. Also, the use of the term "portion" may include part of a moiety or the entire moiety. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, the term "acellular tissue matrix" refers generally to any tissue matrix that is substantially free of native cells. Acellular tissue matrices can be derived from human or xenogenic sources. Acellular tissue matrices may be seeded with exogenous cells derived from the recipient or other sources.

Figure 1:
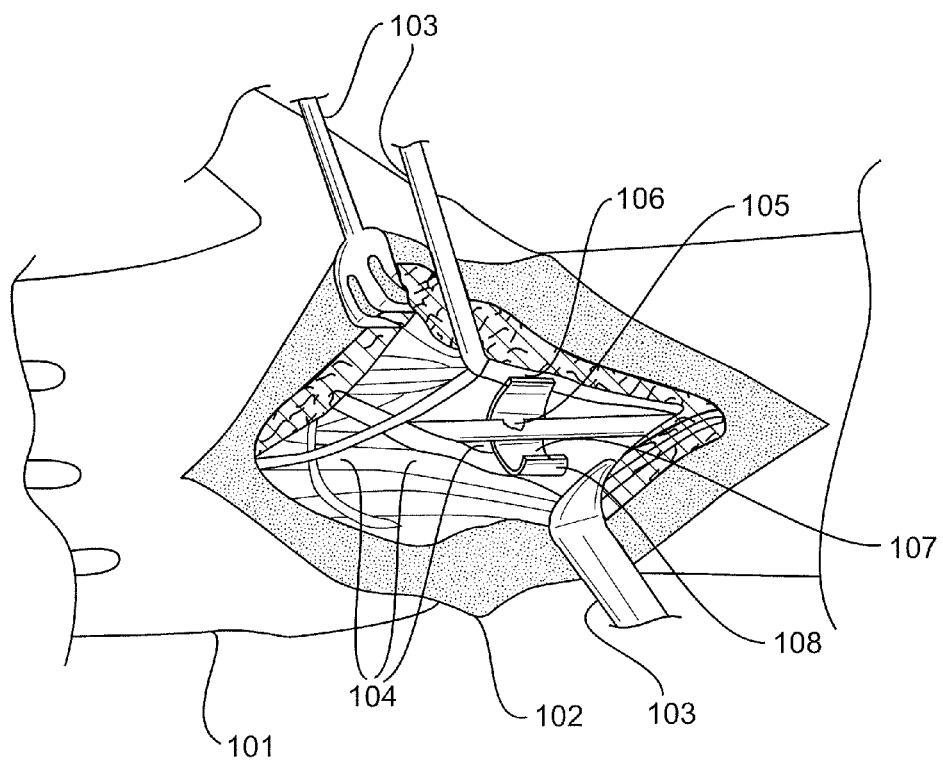
FIG. 1 illustrates a method of treating a tendon or ligament, according to certain embodiments.

FIG. 1 illustrates a method of treating a tendon or ligament, according to certain embodiments. According to certain embodiments, the method comprises selecting a tendon 104 or ligament in need of treatment, and contacting an arterial tissue matrix 106 with at least a portion of the tendon or ligament in need of treatment 105. As described further below, the arterial tissue matrix can include an acellular arterial tissue matrix from which substantially all the native cells have been removed.

Tendons and ligaments are particular types of connective tissue that are composed primarily of fibrous collagen. While tendons connect muscle to bone, ligaments connect bone to bone, as found within a joint. Tendons serve to transmit force generated by the muscles, while ligaments serve to stabilize the associated joint.

In various embodiments, the tissue matrices of the present disclosure can be used to treat a defect in any tendon or ligament. For example, the matrices can be used to treat tendons or ligaments associated with any joint, including the joints of the fingers, wrists, elbows, shoulder, knees, ankles, hips, feet, or any other joint in the body. In some embodiments, the tendon or ligament can be an elongate tubular tendon or ligament, which can be subject to significant tensile stresses. For example, the tendon or ligament can include any tendon, including a rotator cuff tendon, an anterior cruciate ligament, and a flexor or extensor tendon of the hand, wrist, ankle, or foot.

Various defects occurring in tendons and ligaments can be treated with the disclosed methods. A defect may result from various sources, including, but not limited to, an acute or chronic injury, a genetic pre-condition, age, inadequate nutrition, or body weight. These various factors may contribute to defective tissue by either applying excessive force to the tendon or ligament or by serving to weaken their structural properties in some manner. Ligaments are subject to injury when stretched, strained, or stressed beyond their normal range of motion. Defects to tendons and ligaments may include, but are not limited to strains, tears, and gaps. Injuries particular to tendons include tendinitis, i.e., inflammation of the tendon, and tendinosis, in which microtears pervade the connective tissue. In FIG. 1, a defect comprising a tear 105 in a wrist tendon 104 is shown.

The arterial tissue matrix can contact the tendon or ligament in various ways in order to effect treatment. In some embodiments, contacting the tissue comprises positioning the tissue matrix across the area in need of treatment, i.e, the area comprising the defect. In other embodiments, contacting the tissue comprises wrapping the arterial tissue matrix around the area in need of treatment.

The tissue matrices disclosed herein can possess certain attributes that are desirable in the treatment of damaged tendons or ligaments. The disclosed tissue matrix contains elastin, which is found in arterial tissue, as well as collagen. Due to the combination of elastin and collagen within the tissue matrices, the disclosed device is elastic, and able to resume its original shape after being stretched or compressed. The elastic nature of the device also makes it highly resistant to tearing, yet very flexible. The collagen/elastin architecture also confers load-bearing properties to the device.

The disclosed tissue matrix can be used in various ways related to the treatment of tendons or ligaments. The device can provide a protective barrier or conduit around the tendon or ligament, which serves to protect the damaged area from further injury. In some embodiments, the barrier can also prevent scar formation as well as prevent adhesion of outside tissue with the damaged tendon or ligament. When used as a protective barrier, the device can also help prevent fibrosis, in which an excessive amount of fibrous tissue results during the healing process. The barrier may also serve to minimize the loss of growth factors and cytokines released during the healing process, thereby facilitating regeneration of damaged tissue.

Once the tissue matrix has contacted the area of tendon or ligament in need of treatment, various methods can be used to fix the placement of the device. In some embodiments, the tissue matrix is sutured in place. In other embodiments, glue or clips can be used to fix the position of the device. Additional means of fixing the device derived from the surgical or medical arts can also be used in accordance with the claimed method so long as they do not impede the formation of a protective barrier.

In various embodiments, the device disclosed herein can also include a surface comprising an intact basement membrane, a typical component of arterial vessels. The basement membrane is a thin fibrous sheet, composed of basal and reticular lamina, which serves to support the epithelium and endothelium found within the body. Epithelium lines the cavities and surfaces of organs, while endothelium lines the interior surface of blood vessels. In normal arteries, an intact basement membrane lines the interior surface of the artery, also known as the luminal surface.

The presence of an intact basement membrane provides further mechanical support and also provides a smooth surface on one side of the device. When the basement membrane is positioned on the outer surface of the device, its smooth surface prevents adhesion from occurring. This may be desirable when damage to the tendon or ligament is severe and healing requires a longer period of time. In other instances, it may be desirable to position the basement membrane on the interior surface of the device. The positioning of the basement membrane at the interior or exterior surface of the device can be determined as needed.

Figure 2:
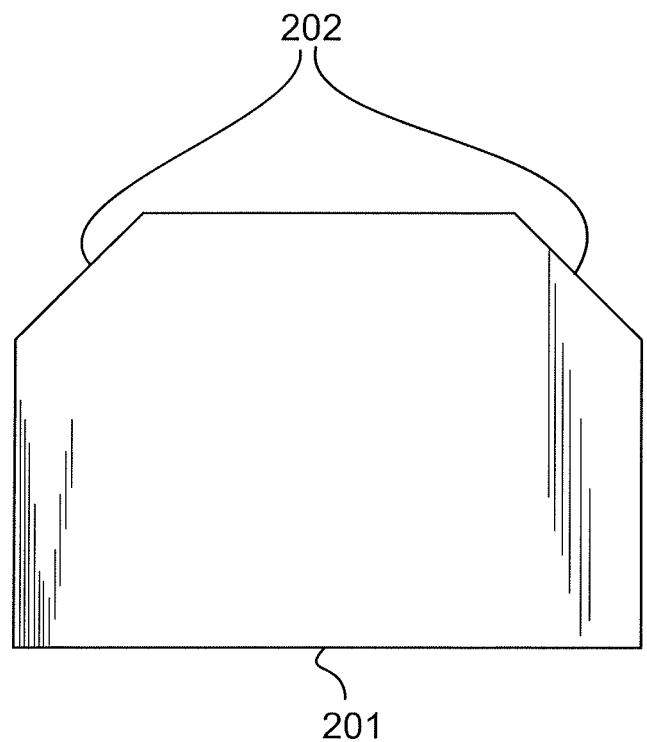
FIG. 2 illustrates a device for treating tendons or ligaments, according to various embodiments.

In various embodiments, an arterial tissue matrix is cut along its length. Prior to cutting, the arterial section has a cylindrical or tubular shape, as it is found in the body. Upon cutting along its length, the arterial section is able to unfurl into a relatively flat, two-dimensional surface, i.e, a sheet. The sheet can be of any shape, such as a circle, square, rectangle, etc., and can be further cut as needed to facilitate certain medical procedures. For example, FIG. 2 illustrates a device 201 for treating tendons or ligaments, according to various embodiments.

In certain embodiments, shapes can be formed with the arterial tissue matrix using various methods. As described further below, partial dehydration can be used to render the tissue matrix more pliable, a mold can be used to provide the desired shape, and irradiation can be used to fix the new shape.

In certain embodiments, a bioactive substance is added to the arterial tissue matrix which further facilitates the repair, regrowth, or regeneration of tendon or ligament. The bioactive substance can be added to the tissue matrix at any point prior to implantation of the tissue matrix in a subject. For example, a bioactive substance can be added during preparation of the device but prior to its storage. In other embodiments, a bioactive substance may be added to the device after storage, but immediately prior to its implantation into a subject. Bioactive substances include, but are not limited to antimicrobial agents, cytokines, growth factors, anti-inflammatory agents, steroids, and corticosteroids. In some embodiments, bioactive substances can include various types of tissue, for example, adipose tissue.

In some embodiments, the bioactive substance comprises cells that facilitate the repair, regrowth, or regeneration of tendon or ligament. In certain embodiments, the acellular tissue matrices can be seeded with stem cells, such as mesenchymal stem cells, including embryonic stem cells and adult stem cells harvested from bone marrow, adipose tissue, and neuronal cells. In other embodiments, autologous stem cells may be used. In some embodiments, allogenic cells can be pre-seeded to the grafts and cultured in vitro and lysed before implantation.

In various embodiments, the tissue matrix can be produced from an arterial section from a variety of different anatomic sites, including, but not limited to, carotid, femoral, ulnar, median, and/or brachial arteries. Furthermore, arterial tissue can be derived from human and/or non-human sources, such as pigs, as described in more detail below. In certain embodiments, the section of artery is selected based on a desired size (e.g., length of defect to be treated and/or approximate tubular diameter of connective tissue to be treated). In various embodiments, the length of the defect can be greater than 1 cm, greater than 2 cm, between 0.1 cm and 1 cm, between 1 cm and 2 cm, greater than 4 cm, greater than 6 cm, greater than 10 cm, or any ranges in between.

As shown in FIG. 2, the device 201 can be shaped to facilitate placement and/or to improve visualization during surgery. For example, as shown, the device 201 can include one or more indentations 202 formed along the corners of the tissue matrix. The indentations can allow improved visualization of the underlying tissue in need of treatment, for example, a tendon 104 with a tear 105. In addition, when the device is wrapped around the damaged tissue with the side comprising the indentations facing up, the surgeon can easily see the extent to which one end of the device overlaps the other, facilitating suturing.

Figure 3:
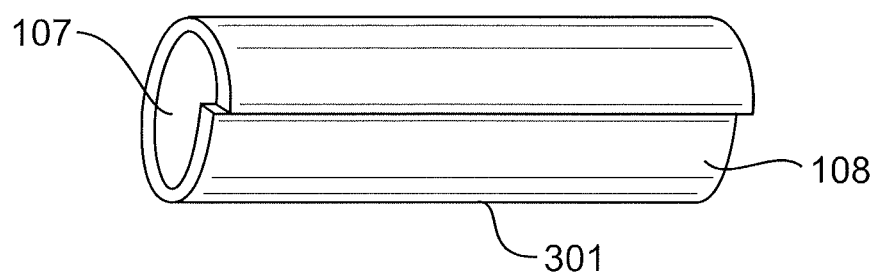
FIG. 3 illustrates a device for treating tendons or ligaments, according to various embodiments.

In certain embodiments, the devices of the present disclosure can be produced with a predefined shape or structure to conform to the anatomic site to be treated. For example, FIG. 3 illustrates a device 301 for treating tendons or ligaments, according to various embodiments. As shown, the device 301 includes a tubular shape, that can be preselected to conform to the shape and/or dimensions of selected ligaments or tendons. In addition, the device 301 can include other features, such as a basement membrane, bioactive substance, or any other properties or structures discussed herein. As discussed previously, the basement membrane can be positioned at the interior surface 107 or exterior surface 108 of the device.

In certain embodiments, a method of preparing a device for treating connective tissue is provided. The method comprises selecting an arterial section, removing substantially all the native cells from the section to obtain an arterial tissue matrix without removing a luminal basement membrane from the arterial section, and cutting the arterial section along its length.

While an acellular tissue matrix may be made from the same species as the acellular tissue matrix graft recipient, different species can also serve as tissue sources. Thus, for example, an acellular tissue matrix may be made from porcine tissue and implanted in a human patient. Species that can serve as recipients of acellular tissue matrix and donors of tissues or organs for the production of the acellular tissue matrix include, without limitation, mammals, such as humans, nonhuman primates (e.g., monkeys, baboons, or chimpanzees), pigs, cows, horses, goats, sheep, dogs, cats, rabbits, guinea pigs, gerbils, hamsters, rats, or mice.

Arterial cellular tissue matrices suitable for use in the present disclosure can be produced by a variety of methods. In various embodiments, the arterial acellular tissue matrices can include various proteins other than collagen, which may support tendon or ligament regeneration. In some embodiments, the matrices can include glycosaminoglycans (GAGs) and/or elastins, which are present in intact arterial tissue. In other embodiments, the matrices can include an intact basement membrane.

Generally, the steps involved in the production of an acellular tissue matrix include harvesting the tissue from a donor (e.g., a human cadaver or animal source) and cell removal under conditions that preserve biological and structural function. In certain embodiments, the process includes chemical treatment to stabilize the tissue and avoid biochemical and structural degradation together with or before cell removal. In various embodiments, the stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and one or more smooth muscle relaxants.

The tissue is then placed in a decellularization solution to remove viable cells (e.g., epithelial cells, endothelial cells, smooth muscle cells, and fibroblasts) from the structural matrix without damaging the biological and structural integrity of the collagen matrix. The decellularization solution may contain an appropriate buffer, salt, an antibiotic, one or more detergents (e.g., TRITON X100™, sodium deoxycholate, polyoxyethylene (20) sorbitan mono-oleate), one or more agents to prevent cross-linking, one or more protease inhibitors, and/or one or more enzymes. In some embodiments, the decellularization solution comprises 0.1% to 10% (w/v) TRITON-X-100™. In other embodiments, the decellularization solution comprises 0.5% to 5% (w/v) TRITON-X-100™. In some embodiments, the decellularization solution comprises 1% TRITON X-100™ in RPMI media with Gentamycin and 25 mM EDTA (ethylenediaminetetraacetic acid). In some embodiments, the tissue is incubated in the decellularization solution overnight at 37° C. with gentle shaking at 90 rpm. In certain embodiments, additional detergents may be used to remove fat from the tissue sample. Additional detergents may comprise sodium deoxycholate in some embodiments. In certain embodiments, the decellularization solution comprises 0.1% to 10% sodium deoxycholate. In other embodiments, 2% sodium deoxycholate is added to the decellularization solution.

It would be understood that variations can be made in the protocol above and still be within the scope of the present invention. For example, other physiological buffers can be utilized so long as they do not impede the decellularization process. In some embodiments, suitable detergents can include, but are not limited to, SDS, sodium cholate, sodium deoxycholate, TRITON-X-100™, and NP40™. The selected detergents can be used at a range of concentrations, for example, from 0.1 to 10% (w/v), 0.5 to 2.0%, 1.0 to 2.0%, 0.1 to 2%, 0.5 to 5%, 0.5 to 10%, 0.1 to 2%, or any values within those ranges.

After the decellularization process, the tissue sample is washed thoroughly with saline. In some exemplary embodiments, e.g., when xenogenic material is used, the decellularized tissue is then treated overnight at room temperature with a deoxyribonuclease (DNase) solution. In some embodiments, the tissue sample is treated with a DNase solution prepared in DNase buffer (20 mM HEPES (4-(2-hydroxyethyl)-1-piperazineethanesulfonic acid), 20 mM $CaCl_2$ and 20 mM $MgCl_2$. In some embodiments, the DNase solution comprises 1 to 100 units/ml DNase. In certain embodiments, the solution comprises 30 units/ml DNase. Optionally, an antibiotic solution (e.g., Gentamicin) may be added to the DNase solution. In some embodiments, the solution comprises 1 to 200 μg/ml gentamicin. In other embodiments, the solution comprises 50 μg/ml gentamicin. Any suitable buffer can be used as long as the buffer provides suitable DNAse activity.

Elimination of the α-gal epitopes from the collagen-containing material may diminish the immune response against the collagen containing material. The α-gal epitope is expressed in non-primate mammals and in New World monkeys (monkeys of South America) as well as on macromolecules such as proteoglycans of the extracellular components. U. Galili et al., *J. Biol. Chem.* 263:17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., *Infect. Immun.* 56:1730 (1988); R. M. Hamadeh et al., *J. Clin. Invest.* 89:1223 (1992).

Because non-primate animals (e.g., pigs) produce α-gal epitopes, xenotransplantation of collagen-containing material from these mammals into primates often results in rejection because of primate anti-gal binding to these epitopes on the collagen-containing material. The binding results in the destruction of the collagen-containing material by complement fixation and by antibody dependent cell cytotoxicity. U. Galili et al., *Immunology Today* 14:480 (1993); M. Sandrin et al., *Proc. Natl. Acad. Sci. USA* 90:11391 (1993); H. Good et al., *Transplant. Proc.* 24:559 (1992); B. H. Collins et al., *J. Immunol.* 154:5500 (1995). Furthermore, xenotransplantation results in major activation of the immune system to produce increased amounts of high affinity anti-gal antibodies. Accordingly, in some embodiments, when animals that produce α-gal epitopes are used as a tissue source, the substantial elimination of α-gal epitopes from cells and from extracellular components of the collagen-containing material, and prevention of cellular α-gal epitope re-expression can diminish the immune response against the collagen-containing material associated with anti-gal antibody binding to α-gal epitopes.

To remove α-gal epitopes, after washing the tissue thoroughly with saline to remove the DNase solution, the tissue sample may be subjected to one or more enzymatic treatments to remove certain immunogenic antigens, if present in the sample. In some embodiments, the tissue sample may be treated with an α-galactosidase enzyme to eliminate α-gal epitopes if present in the tissue. In some embodiments, the enzymatic treatment may comprise 50 to 500 U/L α-galactosidase prepared in a suitable buffer. In some embodiments, the tissue sample is treated with α-galactosidase at a concentration of 200 or 300 U/L prepared in 100 mM phosphate buffer at pH 6.0. In other embodiments, the concentration of α-galactosidase is increased to 400 U/L for adequate removal of the α-gal epitopes from the harvested tissue. Any suitable enzyme concentration and buffer can be used provided adequate removal of antigens is achieved.

Alternatively, rather than treating the tissue with enzymes, animals that have been genetically modified to lack one or more antigenic epitopes may be selected as the tissue source. For example, animals (e.g., pigs) that have been genetically engineered to lack the terminal α-galactose moiety can be selected as the tissue source. For descriptions of appropriate animals, see co-pending U.S. application Ser. No. 10/896,594 and U.S. Pat. No. 6,166,288, the disclosures of which are incorporated herein by reference in their entirety.

As an optional step, the matrix may then be subjected to partial dehydration to facilitate shaping the tissue into a desired form after the tissue matrix has been decellularized and treated to remove certain antigenic epitopes. Partial dehydration of tissues has been found to render the collagen fibers of the tissue matrix more pliable, thus facilitating their reorientation. Excessive means of dehydration such as freeze-drying can render tissues too brittle for further processing and is therefore, undesirable.

A variety of suitable processes can be used to partially dehydrate the arterial tissue matrix. Examples of suitable methods include blot-drying with water-absorbent towels, isothermal water desorption with controlled humidity, application of mechanical forces to tissues, centrifugation, and/or controlled and/or directional freezing. Any method can be used to partially dehydrate the matrix as long as the method does not cause undesirable tissue alterations.

After partial dehydration, mechanical forces can be applied to the arterial matrix to reorient the collagen fibers within the matrix. This can be done in a variety of ways, so long as forces are directed in such a way to produce a final desired shape. In some embodiments, a mold having a desired shape is produced, and a sheet of arterial tissue matrix is placed in contact with the mold. Forces are then applied to portions of the sheet to reorient fibers to a shape consistent with the mold. In certain embodiments, to produce a stable tubular product such as a conduit, a dowel rod or other tubular structure is selected as a mold, and a sheet of arterial tissue matrix is wrapped around the mold.

After the collagen fibers are reoriented, the arterial tissue matrix may be treated to stabilize the new structure. In some embodiments, the structure is stabilized by exposing the matrix to radiation. Radiation may cause a small degree of cross-linking sufficient to produce a stable three-dimensional structure. Excessive cross-linking may alter the biological properties of tissue products and is therefore, undesirable. After irradiation, the stable structure will tend to conform to a shape similar to the mold (or shape of the matrix at the time of irradiation), but will be sufficiently flexible to allow the tissue product to be manipulated during surgery. Suitable forms of radiation include gamma radiation, e-beam radiation, and X-ray radiation.

In various embodiments, the disclosed methods can further comprise additional processing of the device. Such processing of the device may include disinfecting or sterilization the arterial tissue matrix. In some embodiments, the arterial tissue matrix is disinfected with isopropyl alcohol (IPA) (e.g., at about 70% IPA).

The disclosed devices can be further treated to produce aseptic or sterile materials. Accordingly, in various embodiments, the devices can be sterilized after preparation. As used herein, a "sterilization process" can include any process that reduces bioburden in a sample, but need not render the sample absolutely sterile.

Certain exemplary processes include, but are not limited to, a gamma irradiation process, an e-beam irradiation process, ethylene oxide treatment, and propylene oxide treatment. Suitable sterilization processes include, but are not limited to, those described in, for example, U.S. Patent Publication No. 200610073592A1, to Sun et al.; U.S. Pat. No. 5,460,962 to Kemp; U.S. Patent Publication No. 2008/0171092A1, to Cook et al. In some embodiments, sterilization is performed in conjunction with packaging of the device, while in other embodiments, sterilization can occur after packaging. In certain embodiments, sterilization is combined with the fixing step.

After the devices are prepared by the disclosed methods, they may be stored for some time before implantation in or on a patient. In certain embodiments, the device may be packaged in a TYVEK® pouch for storage purposes. The device may also be stored in different states, for example, in a wet state or in a freeze-dried state.

In some embodiments, the device is freeze-dried after preparation. Terminal sterilization by ionizing radiation conducted after freeze-drying, however, can potentially damage freeze-dried tissue. To minimize this damage, the processed material can be packaged wet in moisture-permeable TYVEK® bags first. The tissue is then irradiated in a wet state. After irradiation, the wet samples can be freeze-dried for storage.

Figure 4:
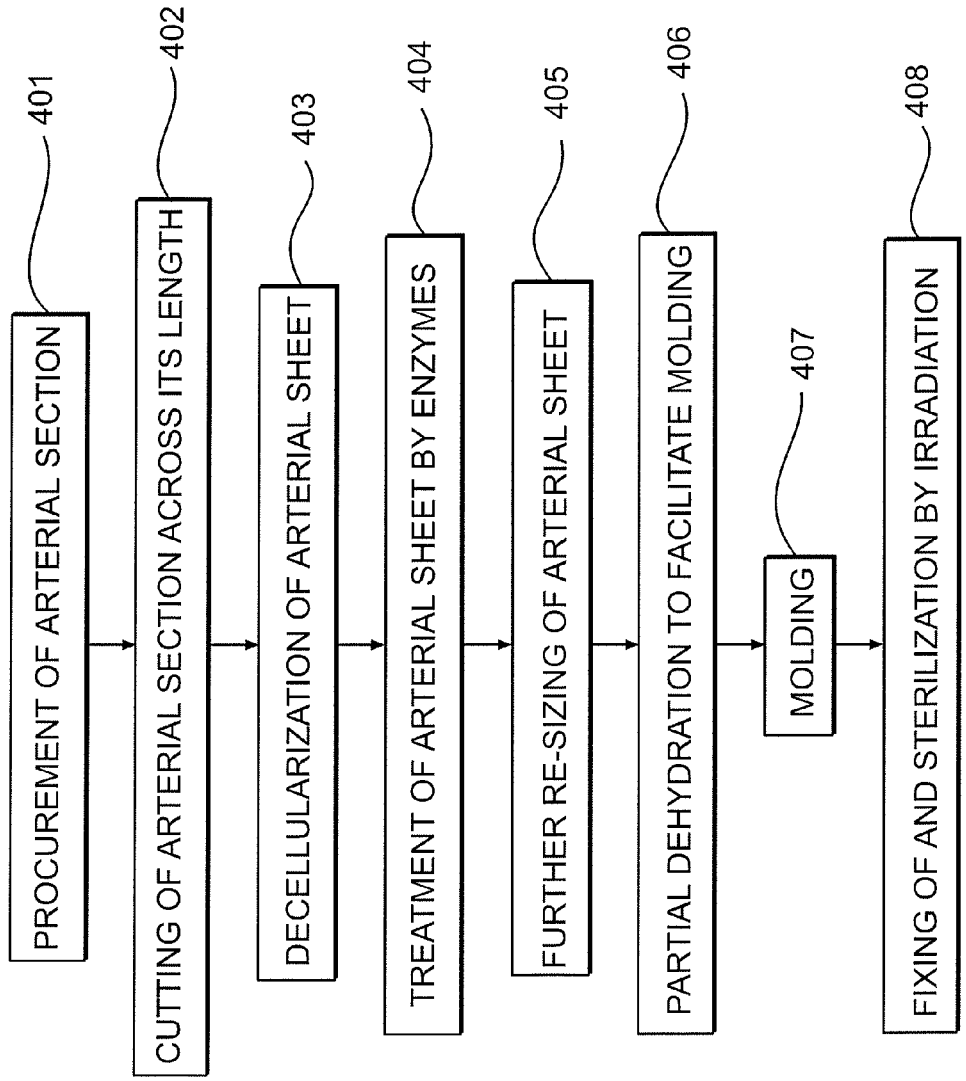
FIG. 4 is a flow chart summarizing the various steps that may be used to produce a device for performing methods of the present disclosure, according to certain embodiments of the disclosed method.

A sample protocol in accordance with the disclosed methods is provided in FIG. 4. The order of certain steps can be changed as needed. Certain steps may also be discarded as necessary. Specific details regarding each step are provided throughout the present disclosure. A section of an arterial vessel is procured from a suitable source 401. The arterial section is still an intact tube at this stage. The arterial section is then cut across its length and unfurled into a sheet 402. The sheet is then incubated in an appropriate solution to decellularize the tissue 403. The sheet is then treated with enzymes to remove DNA and α-gal epitopes 404. After enzyme treatment, the sheet is further re-sized as desired 405. The sheet is then subjected to partial dehydration which facilitates molding of the sheet by rendering it more pliable 406. The sheet is then placed on a mold to provide the sheet with the desired structure 407. During molding, the sheet may be inverted so that the basement membrane of the arterial section constitutes the outer surface of the device. In some embodiments, however, the basement membrane may not constitute the outer surface of the device until it is wrapped around the connective tissue. After the new structure has been achieved, the device is then irradiated to fix the structure 408. In this sample protocol, radiation provided during the fixing step also serves to sterilize the device.

In certain embodiments, devices can be prepared using the following protocol: Porcine carotid arteries are harvested by dissection. After removing blood clots, arteries are then decellularized at room temperature for 24 hours in 1% (w/v) TRITON-X-100™ that was prepared in 10 mM HEPES buffer (pH 8.0) containing 10 mM EDTA. Decellularized arteries are then washed with 0.9% saline to remove the residual detergent until foam is no longer observed. Arteries are then treated for 24 hours in second HEPES buffer solution (10 mM, pH 7.4) containing 30 units/mL DNase, 50 µg/ml gentamicin, 2 mM calcium chloride and 2 mM magnesium chloride. The DNase solution is discarded, and tissue is washed three times with 0.9% saline (10 min each time). Decellularized arteries are further treated in phosphate-buffered saline (pH 6.5) containing 0.2 unit/mL α-galactosidase and 50 mM EDTA to eliminate extracellular α-gal epitope. The artery tissue is then cut to desirable dimensions.

It would be understood that variations can be made in the above protocol and still be in accordance with the present invention. In certain embodiments, for example, biological buffers other than HEPES can be used. Suitable biological buffers can include, but are not limited to, PBS, TBS, and MOPS. Furthermore, the amounts of various buffer components can be altered ad still be in accordance with the present invention. In certain embodiments, the concentration of HEPES buffer (or other buffer such as PBS, TBS, or MOPS) can range from 1 to 100 mM. In certain embodiments, the amount of TRITON-X-100™ can range from 0.1 to 10% (w/v). In certain embodiments, the amount of DNase can range from 1 to 100 units/ml, 1 to 50 units/ml, 1 to 40 units/ml, 4 to 40 units/ml, and 10 to 30 units/ml DNase. In certain embodiments, the buffer comprises 1 to 200 ug/ml gentamicin. In certain embodiments, the amount of calcium chloride and magnesium chloride each may range from 0.1 mM to 100 mM, 0.1 to 50 mM, 1 to 50 mM, 1 to 30 mM, 1 to 10 mM, and 0.1 to 5 mM. In certain embodiments, the amount of α-galactosidase used to remove α-gal epitopes can range from 0.1 to 10 units/ml, 0.1 to 8 units/ml, 0.1 to 5 units/ml, 0.1 to 1 unit/ml, and 0.1 to 0.5 units/ml.

The device prepared by the methods described above can be used in various ways associated with the repair, regrowth, and regeneration of various types of connective tissue, including tendons and ligaments. Methods of treatment using the device include selecting a tendon or ligament in need of treatment, selecting an arterial tissue matrix from which substantially all the native cells have been removed, and contacting the arterial tissue matrix with at least a portion of the tendon or ligament in need of treatment. Connective tissue in need of treatment, including tendons and ligaments in need of treatment, can be readily identified by those skilled in the art, but can include strained or torn tissue, or tissue having a gap, hole, or some other defect. Furthermore, the device can be applied to anywhere tendons and ligaments are found, including, but not limited to shoulders, ankles, elbows, knees, fingers, wrists, and feet.

In some embodiments, positioning the device across the defective tissue comprises wrapping the arterial tissue matrix around the area in need of treatment. Because the arterial section has already been cut into a sheet, it can be wrapped around an injured tendon or ligament. The wrapped sheet forms a protective sheath, tube, or conduit that facilitates the healing process. Without being bound to theory, it is believed that the conduit provides a barrier that minimizes the loss of growth factors or other natural cytokines released during the healing process. Furthermore, the surface of the device comprising the basement membrane can be positioned on the outside or inside of the device. As previously discussed, the basement membrane is typically found on the inside of arteries, providing a smooth surface that facilitates blood flow. In certain instances, however, it may be desirable that the basement membrane is positioned at the outside surface of the device. When placed on the outside, the smooth surface of the basement membrane can be used to prevent adhesion. This may be useful when damage to the connective tissue is relatively severe and will take longer to heal. Once the device has been positioned as desired, it can be held in place using sutures or various biocompatible adhesives, such as fibrin glue.

The placement of the device around a damaged connective tissue is shown in FIG. 1. A human hand 101 has been surgically cut open. The opening in the hand 102 is held open with surgical implements 103, exposing the tendons 104 in the wrist. One of the tendons 104 is in need of treatment, as indicated by a tear 105. A sheet of arterial tissue matrix 106 prepared by the disclosed methods is wrapped around the tear 105. The arterial tissue matrix 106 comprises an interior surface 107, which is adjacent to the tendon 104, and an exterior surface 108. Either the interior surface 107 or exterior surface 108 may comprise the surface with the intact basement membrane, according to certain embodiments. Once the arterial tissue matrix 106 has been wrapped around the tendon 104, the arterial tissue matrix 106 is sutured in place.

What is claimed is:

1. A method for treating a tendon or ligament, comprising:
selecting a tendon or ligament in need of treatment;
selecting an arterial tissue matrix from which substantially all the native cells have been removed, wherein the arterial tissue matrix comprises an intact basement membrane along the luminal side of an artery from which the tissue matrix is produced; and
contacting the arterial tissue matrix with at least portion of the tendon or ligament in need of treatment by wrapping the arterial tissue matrix around the tendon or ligament with the basement membrane facing away from the tendon or ligament.

2. The method of claim 1, wherein contacting the arterial tissue matrix with at least portion of the tendon or ligament in need of treatment comprises wrapping the arterial tissue matrix around the area in need of treatment.

3. The method of claim 1, wherein the arterial tissue matrix comprises a porcine arterial tissue matrix.

4. The method of claim 1, wherein the tendon or ligament is located in an area of the body selected from an ankle, elbow, knee, finger, wrist, shoulder, or foot.

5. The method of claim 1, wherein the tendon or ligament is selected from a rotator cuff tendon, an anterior cruciate ligament, and a flexor or extensor tendon of the hand, wrist, ankle, or foot.

6. The method of claim 1, wherein the tendon or ligament in need of treatment comprises an injury selected from a strain, a tear, or a gap.

7. The method of claim 1, further comprising adding a bioactive substance to the tissue matrix.

8. The method of claim 7, wherein the bioactive substance comprises an antimicrobial agent.

9. The method of claim 7, wherein the bioactive substance comprises a cytokine.

10. The method of claim 7, wherein the bioactive substance comprises a growth factor.

11. The method of claim 7, wherein the bioactive substance comprises adipose tissue.

12. The method of claim 7, wherein the bioactive substance comprises cells.

13. The method of claim 12, wherein the cells comprise stem cells.

14. The method of claim 13, wherein the stem cells comprise mesenchymal stem cells.

15. The method of claim 1, further comprising adding a bioactive substance to the tissue matrix, the bioactive substance comprising one or more of an anti-microbial agent, cells, adipose tissue, growth factors, anti-inflammatory agents, steroids, and corticosteroids.

16. The method of claim 1, wherein the matrix is a porcine matrix.

17. The method of claim 16, wherein the matrix is derived from a pig that has been genetically modified to reduce or eliminate expression of α-1, 3-galactose moieties.

18. The method of claim 17, wherein the pig lacks expression of α-galactosyltransferase.

19. The method of claim 1, wherein the arterial tissue matrix includes elastins present in the arterial section from which the tissue matrix is derived.

* * * * *